United States Patent [19]

Bachmann et al.

[11] Patent Number: 4,620,850

[45] Date of Patent: Nov. 4, 1986

[54] COMPOSITION AND PROCESS FOR THE OXIDATIVE DYEING OF HAIR

[75] Inventors: Heinrich Bachmann, Giffers; Plato Portmann, Fribourg, both of Switzerland

[73] Assignee: Wella Aktiengesellschaft, Darmstadt, Fed. Rep. of Germany

[21] Appl. No.: 641,134

[22] Filed: Aug. 8, 1984

Related U.S. Application Data

[63] Continuation of Ser. No. 253,509, Apr. 8, 1981, abandoned.

[30] Foreign Application Priority Data

Sep. 28, 1979 [DE] Fed. Rep. of Germany ....... 2939304

[51] Int. Cl.$^4$ ................................................ A61K 7/13
[52] U.S. Cl. ............................................ 8/406; 8/423; 549/310
[58] Field of Search ..................... 8/406, 423; 549/310

[56] References Cited

U.S. PATENT DOCUMENTS

| | | | |
|---|---|---|---|
| 3,862,133 | 1/1975 | Layer | 549/310 |
| 4,185,958 | 1/1980 | Bugaut et al. | 8/431 |
| 4,289,495 | 9/1981 | Bugaut et al. | 8/406 |
| 4,453,941 | 6/1984 | Jacobs | 8/424 |

FOREIGN PATENT DOCUMENTS

| | | |
|---|---|---|
| 2836276 | 1/1979 | Fed. Rep. of Germany . |
| 2003137 | 3/1979 | United Kingdom ................ 549/310 |
| 2013728 | 8/1979 | United Kingdom . |

Primary Examiner—Albert T. Meyers
Assistant Examiner—John M. Kilcoyne
Attorney, Agent, or Firm—Michael J. Striker

[57] ABSTRACT

A composition for oxidative dyeing of hair is disclosed, having at least one compound of the general formula

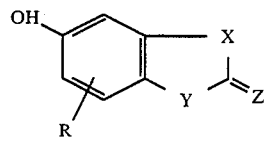

wherein X is $CH_2$, O, S, NH, NR', CH(OH), CHR', $CH(NH_2)$, or $CH(CH_3)$,
Y is O, NH,
Z is O, S, NH,
R is H, OH, R', OR', $NR'_2$, $NO_2$, halogen, and
R' is an alkyl group with one to five carbon atoms.

3 Claims, No Drawings

COMPOSITION AND PROCESS FOR THE OXIDATIVE DYEING OF HAIR

This is a continuation of application Ser. No. 253,509, filed Apr. 8, 1981, now abandoned.

For the dyeing of hair, it is the so-called oxidative colorants that have obtained an essential importance by reason of their being fast to light and washing. To produce the oxidative colorants, certain aromatic compounds capable of oxidative coupling are being applied onto the hair as preliminary coloring stages. These will partially penetrate the hair and be oxidized therein to the desired colorant, either by atmospheric oxygen or, particularly by the addition of chemical oxidants such as hydrogen peroxide.

It is mainly the derivative of diamino or hydroxyamino compounds of benzene, naphthalene, pyridine, pyrimidine, pyrazolone, indol and chinoline, that are serving as preliminary coloring stages. Due partially to physiological reasons, the aforenoted materials are not entirely unobjectionable.

Derivatives of diphenol and naphthol are also known as preliminary coloring stages. However, no intensive hair dyeing could be achieved, so far with representatives of these classes of substances known hitherto as preliminary coloring stages.

Also, as knowledge on the formation of hair pigment was obtained, the use of tyrosine, Dopa[+)], and dihydroxyindolene, for the dyeing of hair has been described. Preparations on the basis of these compounds, which are the most suitable from the physiological aspect for use as preliminary coloring stages, could, however, for various reasons not gain acceptance in practice.

[+)]Dopa=L-$\beta$-(3,4-Dihydroxy-phenyl)alanine.

Numerous particular demands are put forward in respect of oxidative colorants used for dyeing human hair. They must be unobjectionable as to toxicology and dermatology, and allow to obtain colorings to the desired intensity. It is, furthermore, necessary, that a wide spectrum of various coloring nuances can be obtained by a combination of such compounds that are suitable as preliminary coloring stages. In addition, the hair colorings that can be obtained, are required to have good fastness to light and resistance to permanent-wave treatment, acids and rubbing. Such colorings must, at any rate, remain stable against the influence of light, rubbing and chemical agents, for a period of at least four to six weeks.

The plurality of the demands as put forward, are not met to complete satisfaction by the compounds used at present as preliminary coloring stages in oxidative hair dyeing compositions.

The task existed therefore, to prepare compositions for oxidative dyeing of hair, based upon such compounds serving as preliminary coloring stages which, in their physiological aspects, have more suitable properties when compared to known compounds used as preliminary coloring stages. These compounds should, furthermore, possess good fastness to wearing and a sufficient intensity of the colorings, either by themselves or in combination with other compounds known as preliminary coloring stages.

The object of the invention is, therefore, a composition for oxidative dyeing of hair, characterized by containing as preliminary coloring stage, a minimum of one compound of the general formula

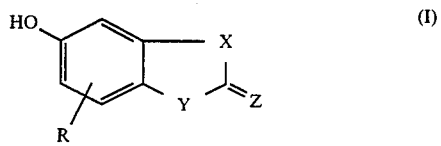

with the following significance:
X=$CH_2$, O, S, NH, NR', CH(OH), CHR', CH($NH_2$), CH($CH_3$)
Y=O, NH
Z=O, S, NH
R=H, OH, R', OR', NR'$_2$, $NO_2$, Halogen
R'=$C_1$- to $C_5$-Alkyl The total content of these compounds serving as preliminary coloring stages as per formula (I) in the compositions discussed herein, should amount to approximately 0.1 to 5 percent by weight, preferably 1 to 4 percent by weight.

Examples for suitable compounds, contained in the hair dyeing compositions as preliminary coloring stages of the aforenamed general formula (I) are, in particular
5-Hydroxy-3H-benzofuran-2-on,
5,6-Dihydroxy-3H-benzofuran-2-on,
5-Hydroxy-6-methyl-3H-benzofuran-2-on,
5-Hydroxy-6-methoxy-3H-benzofuran-2-on,
5-Hydroxy-benzo[1,3]dioxole-2-on
5-Hydroxy-benzo[1,3]dioxole-2-thion
5-Hydroxy-benz[1,3]oxazole-2-on
5-Hydroxy-benz[1,3]oxazole-2-thion
6-Hydroxy-benz[1,3]oxazole-2-on
5-Hydroxy-benzimidazole-2-on
5-Hydroxy-benz[1,3]oxathiol-2-on,
5-Hydroxy-benz[1,3]oxathiol-2-on-imine
5-Hydroxy-benz[1,3]oxathiol-2-thion.

Furthermore, the compositions for dyeing hair of the present application may in particular contain, as preliminary coloring stages, such aromatic compounds as are present in nature, but also other aromatic compounds having a minimum of one hydroxy group in the molecule, and which may additionally have a nitrogen atom or a plurality of nitrogen atoms in the molecule.

Examples for such compounds are:
(a) aromatic compounds containing in the molecules a minimum of one hydroxy group, for example: orcin, hydroquinone, pyrogallol, hydroxy-hydroquinone, protocatechnualdehyde, thymol, guajacol, arbutin, pyrocatechol, juglone, lawsone, flavonoids, grevillines, derivatives of salicylic acid, caffeic acid, chlorogenic acid, pulvinic acid, hydroxy coumarin, as well as
(b) aromatic compounds with a minimum of one hydroxy group and, additionally, a minimum of one hydrogen atom in the molecule, such as: 3-hydroxyanthranilic acid kynurenic acid, xanthurenic acid, Dopa, tyrosine, and also derivatives of anthranilic acid, nicotinic acid, isonicotinic acid, pyrrol, picolinic acid, kynurenin, of ommatins, pyrimidines and purines.

These compounds may be used in a ratio of 0.1 to 1 mol relative to 1 mol of the compounds of the general formula (I) contained herein as preliminary coloring stages.

The total quantity of compounds serving as preliminary coloring stages in the hair dyeing compositions as per invention, will suitably amount to approximately 0.1 to 5 percent by weight, preferably 1 to 4 percent by weight.

It is furthermore possible for the hair dyeing compositions, additionally to contain usual direct-acting hair colorants. To increase the coloring depth of the hair colorings, the dyeing compositions as per the present application may furthermore contain amino acids occurring in nature, their esters with lower alcohols of 1 to 5 carbon atoms and/or their amides, as well as mono or dialkyl amides.

Examples therefor are the following amino acids: glycine, proline, serine, cysteine, histidine and tryptophane, their esters with lower alcohols, as well as their respective amides or mono or dialkyl amides, wherein the alkyl group at the nitrogen of the amide will have 1 to 5 carbon atoms.

The amino acids and their aforenamed derivatives may be contained in the compositions particularly in a proportion of 0.05 to 1 mol relative to 1 mol of the compounds present therein as preliminary coloring stages.

To accelerate oxidation of the compounds contained as preliminary coloring stages in the hair dyeing compositions as per invention, the compositions may additionally contain small quantities of redox catalysts, particularly glycine copper, in a quantity of approximately 0.01 to 0.1 percent by weight.

Finally, there may furthermore be present in the hair dyeing compositions usual cosmetic additives, for instance antioxidants such as ascorbic acid or sodium sulfite, alkalizing agents such as alkali hydroxides, ammonium or, respectively, alkali carbonate and ammonium or, respectively, alkali hydrogen carbonates, organic acids such as acetic acid, lactic acid and citric acid, solvents, perfumes, swelling agents, wetting agents, emulgators, thickeners, hair-care substances and others.

The preparation may be made available as a solution, preferably, however as a cream, a gel or an emulsion. Its composition will represent a mixture of the colorant constituents with such constituents as usual in such preparations. The usual constituents of creams, gels or emulsions coming into consideration will, for instance, be wetting agents or emulgators from the categories of anionic, cationic or noniongenic surfactants such as sulfates of fatty alcohols, alkyl sulfonates, alkylbenzene sulfonates, salts of alkyl trimethylammonium, oxethylated fatty alcohols, oxethylated nonylphenols, fatty acid alkanol amides and, furthermore, thickeners such as higher fatty alcohols, starch, cellulose derivatives, paraffin oil and fatty acids, and, furthermore, hair-care substances such as lanolin derivatives, cholesterol and pantothenic acid.

The constituents are noted, are used in quantities usual for these purposes, i.e. wetting agents and emulgators in concentrations of approximately 0.5 to 30 percent by weight, while thickeners may be present in the preparations in a quantity of approximately 0.1 to 25 percent by weight.

The dyeing compositions as per invention may react weakly acidic, neutral or alkaline. They are, in particular, of a pH value in the acidic range of 2 to 4, and in the alkaline range of 7 to 8.5, adjustment being preferably made with, respectively, an organic acid or ammonia, or ammonium hydrogen carbonate, For setting an alkaline pH value, use may also be made of organic amines such as f.i., mono or triethanolamines.

In the process for oxidative dyeing of hair as per invention, one proceeds in such a manner that in the first stage a hair dyeing composition of preferably weakly acidic or alkaline setting containing as preliminary coloring stage a minimum of one compound of the general formula

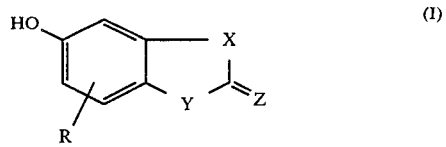

and of the significance
$X = CH_2$, O, S, NH NR', CH(OH), CHR', $CH(NH_2)$, $CH(CH_3)$
Y = O, NH
Z = O, S, NH
R = H, OH, R', OR', $NR'_2$, $NO_2$, Halogen
R' = $C_1$- to $C_5$-Alkyl is uniformly applied onto the hair, allowed to act for about 10 to 20 minutes at a temperature of 20° to 40° C., and then applying in the second step either (a) with alkaline setting of the hair dyeing composition, a 1 to 8 percent alkaline solution of a suitable oxidant, preferably hydrogen peroxide or ammonium peroxodisulfate, allowing it to act upon the hair for a further 10 to 20 minutes at identical temperature or, (b) with a hair dyeing composition of acidic setting, applying a correspondingly neutral oxidant solution onto the hair, allowing it to act for about 5 to 15 minutes and, in given instances, subsequently applying an alkaline agent, preferably in the form of a 5 to 10 percent ammonia solution which is allowed to act for approximately 15 minutes, and furthermore, if the hair had been subjected to an alkaline solution, rinsing it in a third stage, first with an aqueous solution of a weak organic acid, preferably citric acid containing if necessary EDTA+), and finally, in all instances, washing out with water.

+)EDTA = Ethylenediaminetetraacetate

Of particular significance herein is the technological progress achieved in respect of dermatology and toxicology by the use of compounds of the general formula

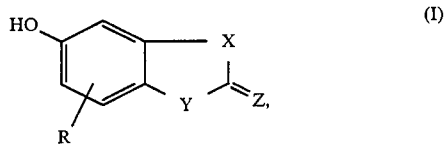

with the significance of
$X = CH_2$, O, S, NH, NR', CH(OH), CHR', $CH(NH_2)$, $CH(CH_3)$
Y = O, NH
Z = O, S, NH
R = H, OH, R', OR', $NR'_2$, $NO_2$, Halogen
R' = $C_1$- to $C_5$-Alkyl, as preliminary coloring stage in the hair dyeing compositions described herein; this particularly valid when compared with such known compounds serving as preliminary color stage, that have an amino group in the molecule. For instance, the 5-hydroxy-3H-benzofuran-2-on is, upon resorption in the body, converted by hydrolysis into homogentisic acid which, at any rate, is present in the human metabolism, and non-objectionable as to toxicology.

The hair dyeing agent as per invention will, furthermore, result in stable colorings of a natural effect, and generally achieve deeper coloring nuances than when using di or polyphenols.

The following embodiments shall explain the object of the invention in more detail.

EMBODIMENTS

| Embodiment 1 | |
|---|---|
| 1.60 g | 5-Hydroxy-3H—benzofuran-2-on |
| 0.80 g | Protocatechualdehyde |
| 0.40 g | Glycine amide |
| 0.40 g | Tryptophane methyl ester |
| 0.40 g | Dopa |
| 0.03 g | Glycine copper |
| 1.00 g | Hydroxyethylcellulose, medium viscosity |
| 9.50 g | Guanidine hydrochloride |
| 2.00 g | Ammonium hydrogencarbonate |
| 40.00 g | Ethanol |
| 43.87 g | Water |
| 100.00 g | |

This hair dyeing composition, having a pH value of 7.8, is applied onto untreated blond human hair, and allowed to act thereon for 15 minutes at a temperature of 25° C. Subsequently, 50 mL of an aqueous solution of 6 percent by weight ammonia, and 1.5 percent by weight hydrogen peroxide, are applied onto the hair. This solution is also allowed to act for 15 minutes at the same temperature. The hair is then first rinsed with a 10% solution of citric acid containing also 0.05 percent by weight EDTA, and finally re-rinsed with water. The hair has obtained a brownish-orange coloring.

| Embodiment 2 | |
|---|---|
| 1.60 g | 5-Hydroxy-3H—benzofuran-2-on |
| 0.40 g | Anthranilic acid methylester |
| 0.40 g | Glycine methylester |
| 0.40 g | Tryptophane methylester |
| 0.03 g | Glycine copper |
| 1.00 g | Hydroxyethylcellulose, medium viscosity |
| 9.50 g | Guanidine hydrochloride |
| 2.00 g | Acetic acid |
| 40.00 g | Ethanol |
| 44.67 g | Water |
| 100.00 g | |

This hair dyeing composition in gel form is applied onto bleached human hair and allowed to act for 15 minutes at a temperature of 25° C. Subsequently, 50 mL of a 5 percent solution of ammonium peroxodisulfate are uniformly distributed over the hair and allowed to act for a further 15 minutes at the same temperature. The hair is finally thoroughly rinsed with water. The hair has obtained a bright grayish-brown coloring.

EMBODIMENT 3

A hair dyeing composition of the composition as per embodiment 2, is applied onto bleached human hair and allowed to act for 15 minutes at a temperature of 25° C. Subsequently, 50 mL of a 5% solution of ammonium peroxodisulfate are applied and allowed to act for 10 minutes. Thereupon, 20 mL of a 9% solution of ammonia are applied onto the hair and allowed to act for 15 minutes. Finally, the hair is first rinsed with a 10% aqueous solution of citric acid containing 0.05% EDTA and then re-rinsed with water. The hair has obtained a chestnut-brown coloring.

| Embodiment 4 | |
|---|---|
| 3.00 g | 5-Hydroxy-benzo[1,3]dioxol-2-on |
| 0.80 g | Glycine amide |
| 1.00 g | Hydroxyethylcellulose, medium viscosity |
| 9.50 g | Guanidine hydrochloride |
| 0.03 g | Glycine copper |
| 2.00 g | Ammonium hydrogencarbonate |
| 25.00 g | Ethanol |
| 58.67 g | Water |
| 100.00 g | |

This hair dyeing composition, set with ammonium carbonate solution to a pH value of 7.5, is applied onto light-blond human hair and allowed to act for 15 minutes at a temperature of 25° C. Subsequently, 50 mL of an aqueous solution of 3 percent by weight of ammonia and 5 percent by weight of ammonium peroxodisulfate, are applied onto the hair. 15 minutes are allowed for activity at the same temperature. The hair is then first rinsed with a 10% solution of citric acid containing also 0.05 percent by weight of EDTA, and finally re-rinsed with water. The hair has obtained a darkish black-brown coloring.

| Embodiment 5 | |
|---|---|
| 1.60 g | 5-Hydroxy-benz[1,3]oxazole-2-on |
| 1.60 g | 5-Hydroxy-benz[1,3]oxathiol-2-on |
| 0.80 g | Orcin |
| 0.40 g | Glycine amide |
| 0.40 g | Cysteine methylester |
| 1.00 g | Hydroxyethylcellulose, medium viscosity |
| 9.50 g | Guanidine hydrochloride |
| 0.03 g | Glycine copper |
| 2.00 g | Ammonium hydrogencarbonate |
| 82.67 g | Water |
| 100.00 g | |

This hair dyeing composition, having a pH value of 7.6, is applied onto bleached hair and allowed to act for 15 minutes at a temperature of 25° C. Thereupon, 50 mL of an aqueous solution containing 6 percent by weight ammonia, and 1.5 percent by weight of hydrogen peroxide, are applied and also allowed to act for 15 minutes. Finally, the hair is first rinsed with a 10% solution of citric acid containing 0.05 percent by weight EDTA, and re-rinsing is then made with water. The hair has obtained a golden-blond coloring. All percentages quoted in the present application represent percent by weight.

We claim:

1. A process for the oxidative dyeing of human hair, comprising the steps of applying an amount sufficient for dyeing the hair of a composition for oxidative dyeing of human hair comprising 0.1 to 5.0% by weight of a compound of the general formula

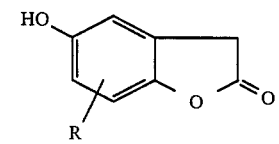

wherein

R represents H, OH, R' or OR', and

R' represents an alkyl group having 1-5 carbon atoms, and the usual cosmetic additives for hair dyeing, with a pH value of 7.0-8.5 onto the hair, allowing the hair dyeing composition to remain on the hair for approximately 10-20 minutes at a temperature of 20°-40° C., applying an amount sufficient for oxidizing the compound of formula (i) of an approximately 1-8% alkaline solution of hydrogen peroxide or ammonium peroxodisulfate, leaving the solution on the hair for a further 10-20 minutes at the same temperature, and washing the hair with water.

2. The process according to claim 1, wherein the composition for oxidative dyeing of human hair further comprises 0.1-1 mol relative to 1 mol of the compound of formula (i) of at least one compound selected from the group consisting of orcin, hydroquinone, pyrogallol, hydroxyhydroquinone, protocatechualdehyde, thymol, guajacol, arbutin, pyrocatechol, juglone, lawsone, caffeic acid, chlorogenic acid, pulvinic acid, hydroxycoumarin, 3-hydroxy-anthranilic acid, kynurenic acid, xanthurenic acid, dopa and tyrosine.

3. A process for the oxidative dyeing of human hair, comprising the steps of applying an amount sufficient for dyeing the hair of a composition for oxidative dyeing of human hair comprising 0.1-5.0% by weight of a compound of the general formula

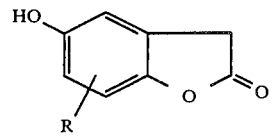

wherein

R represents H, OH, R' or OR', and

R' represents an alkyl group having 1-5 carbon atoms, and the usual cosmetic additives for hair dyeing, with a pH value of 2-4, onto the hair, allowing the hair dyeing composition to remain on the hair for approximately 10-20 minutes at a temperature of 20°-40° C., applying onto the hair a neutral solution of hydrogen peroxide or ammonium peroxodisulfate in an amount sufficient for oxidizing the compound of formula (i), leaving said solution on the hair for approximately 5-15 minutes, applying onto the hair a 5-10% ammonia solution, leaving the solution on the hair for approximately 15 minutes, and washing the hair with water.

* * * * *